(12) United States Patent
Ravikumar et al.

(10) Patent No.: US 10,221,115 B2
(45) Date of Patent: Mar. 5, 2019

(54) METHODS AND SYSTEM FOR DECREASING GAS EMISSIONS FROM LANDFILLS

(71) Applicant: Fluor Technologies Corporation, Sugar Land, TX (US)

(72) Inventors: Ravi Ravikumar, Lancaster, CA (US); Jim Wilson, Buck Hill Falls, PA (US); Denny Li, Aliso Viejo, CA (US)

(73) Assignee: Fluor Technologies Corporation, Sugar Land, TX (US)

(*) Notice: Subject to any disclaimer, the term of this patent is extended or adjusted under 35 U.S.C. 154(b) by 303 days.

(21) Appl. No.: 15/068,748

(22) Filed: Mar. 14, 2016

(65) Prior Publication Data
US 2016/0194262 A1    Jul. 7, 2016

Related U.S. Application Data

(60) Continuation-in-part of application No. 14/836,495, filed on Aug. 26, 2015, which is a division of
(Continued)

(51) Int. Cl.
*C07C 29/151*  (2006.01)
*C07C 29/32*   (2006.01)
(Continued)

(52) U.S. Cl.
CPC .......... *C07C 29/1518* (2013.01); *B01D 17/00* (2013.01); *C07C 29/32* (2013.01);
(Continued)

(58) Field of Classification Search
CPC ...... C07C 29/1518; C07C 31/02; C10J 3/721; C10J 3/485; C10J 2300/0946;
(Continued)

(56) References Cited

U.S. PATENT DOCUMENTS

| 3,064,029 A | 11/1962 | Clarence et al. |
| 3,950,369 A | 4/1976  | Gent |

(Continued)

FOREIGN PATENT DOCUMENTS

| EP | 0253540 A1 | 1/1988 |
| EP | 1916233 A1 | 4/2008 |

(Continued)

OTHER PUBLICATIONS

Patent Cooperation Treaty, "Notification of Transmittal of the International Search Report and the Written Opinion of the International Searching Authority, or the Declaration", PCT Application No. PCT/US/2013/041698, dated May 17, 2013.
(Continued)

*Primary Examiner* — Jafar F Parsa
(74) *Attorney, Agent, or Firm* — Conley Rose, PC

(57) ABSTRACT

A method of diverting municipal solid waste (MSW) from a landfill that includes receiving, at a MSW processing system, a quantity of MSW, gasifying the quantity of MSW in a gasification unit to yield a syngas stream and biochar stream, converting at least a portion of the syngas to mixed alcohols in an alcohol synthesis unit, separating the mixed alcohols into one or more alcohol products, and determining a carbon offset for diverting the MSW from the landfill to the MSW processing system.

18 Claims, 5 Drawing Sheets

Related U.S. Application Data application No. 13/474,452, filed on May 17, 2012, now Pat. No. 9,149,739.

(51) Int. Cl.
| | |
|---|---|
| *B01D 17/00* | (2006.01) |
| *C10K 1/00* | (2006.01) |
| *C10G 2/00* | (2006.01) |
| *C10J 3/64* | (2006.01) |
| *C10J 3/46* | (2006.01) |
| *C10J 3/82* | (2006.01) |
| *G06Q 40/00* | (2012.01) |
| *G06Q 30/00* | (2012.01) |

(52) U.S. Cl.
CPC ........ *C10G 2/32* (2013.01); *C10J 3/64* (2013.01); *C10J 3/82* (2013.01); *C10K 1/004* (2013.01); *C10K 1/005* (2013.01); *G06Q 30/018* (2013.01); *G06Q 40/00* (2013.01); *C10J 3/466* (2013.01); *C10J 2200/09* (2013.01); *C10J 2300/093* (2013.01); *C10J 2300/0906* (2013.01); *C10J 2300/0909* (2013.01); *C10J 2300/0916* (2013.01); *C10J 2300/0943* (2013.01); *C10J 2300/0946* (2013.01); *C10J 2300/0973* (2013.01); *C10J 2300/1659* (2013.01); *C10J 2300/1665* (2013.01); *C10J 2300/1675* (2013.01); *C10J 2300/1807* (2013.01); *Y02E 50/18* (2013.01); *Y02E 50/32* (2013.01); *Y02E 50/346* (2013.01); *Y02P 20/145* (2015.11)

(58) Field of Classification Search
CPC .......... C10J 2300/976; C10J 2300/1643; C10J 2300/1815; C10J 2300/1675; C10J 2300/0906; Y02E 50/32; Y02E 50/18; Y02P 30/10; Y02P 30/20
See application file for complete search history.

(56) References Cited

U.S. PATENT DOCUMENTS

| | | | |
|---|---|---|---|
| 7,638,070 | B2 | 12/2009 | Johnson et al. |
| 7,781,490 | B2 | 8/2010 | Lattner et al. |
| 7,857,995 | B2 | 12/2010 | Johnson et al. |
| 7,968,006 | B2 | 6/2011 | Johnson et al. |
| 8,017,040 | B2 | 9/2011 | Johnson et al. |
| 8,017,041 | B2 | 9/2011 | Johnson et al. |
| 8,021,577 | B2 | 9/2011 | Johnson et al. |
| 8,197,698 | B2 | 6/2012 | Johnson et al. |
| 8,629,188 | B2 | 1/2014 | Ravikumar et al. |
| 9,149,739 | B2 | 10/2015 | Ravikumar et al. |
| 2001/0020044 | A1* | 9/2001 | Whitney ............. C07C 29/1518 518/703 |
| 2002/0016375 | A1 | 2/2002 | Iijima et al. |
| 2003/0014974 | A1 | 1/2003 | Rojey et al. |
| 2003/0203983 | A1 | 10/2003 | ORear et al. |
| 2004/0244289 | A1 | 12/2004 | Morozumi et al. |
| 2004/0248999 | A1 | 12/2004 | Briscoe et al. |
| 2007/0010589 | A1 | 1/2007 | Pearson |
| 2007/0011945 | A1 | 1/2007 | Grootveld et al. |
| 2007/0259972 | A1* | 11/2007 | Lattner ................. C07C 1/20 518/700 |
| 2008/0098654 | A1 | 5/2008 | Cherry et al. |
| 2009/0048354 | A1 | 2/2009 | Bell et al. |
| 2009/0069452 | A1 | 3/2009 | Robota |
| 2010/0018113 | A1* | 1/2010 | Bohlig ................. C10J 3/463 44/550 |
| 2010/0018217 | A1 | 1/2010 | Boshoff et al. |
| 2010/0069514 | A1 | 3/2010 | Gracey et al. |
| 2010/0175320 | A1 | 7/2010 | Schuetzle et al. |
| 2010/0285576 | A1 | 11/2010 | Norbeck et al. |
| 2010/0286292 | A1 | 11/2010 | Wix |
| 2011/0054231 | A1 | 3/2011 | Peterson |
| 2011/0144397 | A1 | 6/2011 | van Egmond et al. |
| 2011/0178185 | A1* | 7/2011 | Blevins ............... C07C 29/1518 518/700 |
| 2011/0201701 | A1* | 8/2011 | Lucas ................. C07C 29/1518 518/702 |
| 2015/0361015 | A1 | 12/2015 | Ravikumar et al. |
| 2016/0194262 | A1 | 7/2016 | Ravikumar et al. |

FOREIGN PATENT DOCUMENTS

| | | |
|---|---|---|
| WO | 2005/021421 A2 | 3/2005 |
| WO | WO2011066074 A2 | 6/2011 |
| WO | WO2013044134 A2 | 3/2013 |
| WO | WO2013173787 A1 | 11/2013 |

OTHER PUBLICATIONS

Restriction Requirement dated Jul. 3, 2014, U.S. Appl. No. 13/474,452, filed May 17, 2012.
Final Office Action dated Dec. 4, 2014, U.S. Appl. No. 13/474,452, filed May 17, 2012.
Notice of Allowance dated Aug. 26, 2015, U.S. Appl. No. 13/474,452, filed May 17, 2012.
Office Action dated Oct. 30, 2017, U.S. Appl. No. 14/836,495, filed Aug. 26, 2015.
Notice of Allowance dated Apr. 10, 2018, U.S. Appl. No. 14/836,495, filed Aug. 26, 2015.
Restriction Requirement dated Jun. 28, 2013, U.S. Appl. No. 13/624,699, filed Sep. 21, 2012.
Notice of Allowance dated Sep. 11, 2013, U.S. Appl. No. 13/624,699, filed Sep. 21, 2012.
International Search Report and Written Opinion of the International Searching Authority, or the Declaration dated Aug. 30, 2013, PCT Application No. PCT/US2013/041698, filed May 17, 2013.
International Preliminary Report on Patentability dated Nov. 17, 2014, PCT Application No. PCT/US2013/041696, filed May 17, 2013.
International Search Report and Written Opinion of the International Searching Authority, or the Declaration dated Mar. 22, 2013, PCT Application No. PCT/US2012/056713, filed Sep. 21, 2012.
International Preliminary Report on Patentability dated Mar. 25, 2014, PCT Application No. PCT/US2012/056713, filed Sep. 21, 2012.
Guetiel, R. et al., "Reactors for Fischer-Tropsch Synthesis" Chemical Engineering Technology, 2008, vol. 31, No. 5, pp. 746-754.
Ravikumar, Ravi, et al., "Carbon Neutral Natural Gas to Liquids Plant With Biomass Co-Feed," filed Sep. 21, 2011, U.S. Appl. No. 61/538,502.

* cited by examiner

METHODS AND SYSTEM FOR DECREASING GAS EMISSIONS FROM LANDFILLS

CROSS-REFERENCE TO RELATED APPLICATIONS

The subject matter disclosed herein is related generally to the subject matter disclosed in U.S. patent application Ser. No. 14/836,495, filed on Aug. 26, 2015, and entitled "Production of Higher Alcohols with Minimum Methanol Content from the Gasification of Carbonaceous Materials" and to U.S. Pat. No. 9,149, 739, issued on Oct. 6, 2015, and entitled "Production of Higher Alcohols with Minimum Methanol Content from the Gasification of Carbonaceous Materials", which are incorporated herein by reference in their entirety.

FIELD OF INVENTION

The subject matter disclosed herein relates to systems and methods for the diversion of gas producing materials from landfills and, more particularly, for decreasing the emission of one or more gases from landfills. The subject matter disclosed herein also relates to systems and methods for generating a carbon credit (e.g., a carbon offset), more particularly, for quantifying and claiming a carbon credit based upon a decrease in the production of one or more gases from a landfill.

BACKGROUND

Each year in the United States, nearly 150 million tons of Municipal Solid Waste (MSW) is sent to landfills—nearly 440,000 tons each day. Disposing of such voluminous amounts of MSW in landfills removes valuable land from other potential uses. Further, landfills are a potential source of soil and groundwater contamination, a disruption to wildlife, and are costly to operate. Moreover, landfills are known to produce gases as a result of the anaerobic digestion by microbes of the MSW.

Landfill gas is a mixture of different gases as a result of the action of microorganisms within a landfill, for example, methanogenesis. The major components are carbon dioxide and methane, which are greenhouse gases (GHGs). GHGs are gases in the earth's atmosphere that absorb and emit radiation within the thermal infrared range. As such, landfill gas has the potential to impact climate change; many believe that $CH_4$ released into the atmosphere has at least twenty times the harmful effect of carbon dioxide. As such, what is needed is a way in which to decrease reliance upon landfills and, thereby, decrease the occurrence of landfill gases.

Also, the 2010 United States federal budget proposes to support clean energy development with a 10-year investment of $15 billion per year, generated from the sale of GHG emissions credits. Emissions trading schemes are a market-based approach used to control pollution by providing economic incentives for achieving reductions in the emissions of pollutants. Governing entities may establish a limit or cap on the amount of a pollutant that can be emitted. Such limit or cap may be applied, allocated, or sold to entities which have been identified as capable of producing emissions at a level which could be subject to the established limit or cap for said designated pollutants. These limits or caps may be applied, allocated, or sold to such emissions entities in the form of emissions permits which represent the right to emit or discharge a specific volume of a specified pollutant. Such emission producing entities are required to hold a number of permits (or credits) equivalent to their emissions. The total amount of permits (or credits) issued by the governing entity cannot exceed the cap; thus, limiting total emissions to that level. Emissions entities that need to increase their level of emissions must buy permits from those who require fewer permits. The transfer of permits is referred to as a trade. In effect, the buyer is paying a charge for polluting, while the seller is being rewarded for having reduced emissions.

The overall goal of an emissions trading plan is to minimize the cost of meeting a set emissions target. The cap is an enforceable limit on emissions that is usually lowered over time–aiming towards a national emissions reduction target. In other systems, a portion of all traded credits must be retired, causing a net reduction in emissions each time a trade occurs. Thus, in theory, by limiting or capping polluting emissions the totality of pollution may be decreased. Moreover, those who can reduce emissions most cheaply will do so, achieving pollution reduction at the lowest cost to society.

Therefore, emissions trading schemes create a framework by which a carbon offset may be utilized as a carbon credit. A "carbon offset" generally refers to a reduction by an entity in emissions of carbon dioxide or another GHG that is capable of compensating for an emission of carbon dioxide or another GHG elsewhere. Carbon offsets are measured in metric tons of carbon dioxide-equivalent ($CO_2e$) and include various categories of GHGs, among them, carbon dioxide and methane. One carbon offset represents the reduction of one metric ton of carbon dioxide or its equivalent in other greenhouse gases. A "carbon credit" generally refers to a tradable certificate, permit, or other negotiable instrument representing the right to emit one ton of carbon dioxide or the mass of another greenhouse gas having a carbon dioxide equivalency of one metric ton, There are active trading programs in several air pollutants including carbon credits. Thus, a system or method that may be operated so as to yield an overall reduction in emissions in the amount of carbon dioxide or an equivalent GHG may be economically beneficial.

SUMMARY

Disclosed herein is an embodiment of a method of diverting municipal solid waste (MSW) from a landfill comprising receiving, at a MSW processing system, a quantity of MSW, gasifying the quantity of MSW in a gasification unit to yield a syngas stream and biochar stream, converting at least a portion of the syngas to mixed alcohols in an alcohol synthesis unit, separating the mixed alcohols into one or more alcohol products, and determining a carbon offset for diverting the MSW from the landfill to the MSW processing system.

Also disclosed herein is an embodiment of a method of diverting municipal solid waste (MSW) from a landfill comprising receiving, at a MSW processing system, a quantity of MSW, gasifying the quantity of MSW in a gasification unit to yield a syngas stream and a biochar stream, converting at least a portion of the syngas to a hydrocarbon product stream, wherein the hydrocarbon product stream comprises liquid hydrocarbons, and determining a carbon offset for diverting the MSW from the landfill to the MSW processing system.

Also disclosed herein is an embodiment of a method comprising receiving a feed stream of municipal solid waste (MSW), optionally drying the MSW, gasifying a quantified amount of the MSW in a gasification unit and recovering a syngas product stream and a biochar product stream, wherein the gasified MSW has a landfill methane equivalent, generating a negotiable credit based upon the landfill methane equivalent of the quantified amount of gasified MSW, optionally altering a hydrogen to carbon monoxide ratio of at least a portion of the syngas product stream, converting at least a portion of the syngas to mixed alcohols or Fischer-Tropsch (FT) liquids, and separating the mixed alcohols or Hliquids into one or more salable products.

Also disclosed herein is an embodiment of a method comprising receiving a feed stream of municipal solid waste (MSW), optionally drying the MSW, gasifying a quantified amount of the MSW in a gasification unit and recovering a syngas product stream and a biochar product stream, calculating a negotiable credit based upon a landfill methane equivalent of the quantified amount of the gasified MSW, optionally altering a hydrogen to carbon monoxide ratio of at least a portion of the syngas product stream, converting at least a portion of the syngas to mixed alcohols or FT liquids, and separating the mixed alcohols or FT liquids into one or more salable products.

Also disclosed herein is an embodiment of a method comprising receiving a feed stream of municipal solid waste (MSW), drying the MSW to produce dried MSW, gasifying a quantified amount of the dried MSW in a gasification unit and recovering a syngas product stream and a biochar product stream, calculating a negotiable credit based upon a landfill methane equivalent of the gasified MSW, altering a hydrogen to carbon monoxide ratio of at least a portion of the syngas product stream and recovering a hydrogen product stream and an adjusted syngas stream, feeding at least a portion of the adjusted syngas to a mixed alcohols production unit to produce mixed alcohols, recycling carbon dioxide from the mixed alcohols production unit to the gasification unit, and separating the mixed alcohols into one or more salable products.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Disclosed herein are embodiments of systems and methods for lessening the production of landfill gases. More particularly, disclosed herein are embodiments of systems and methods for diverting MSW from a landfill to a MSW processing (MSWP) system. The MSWP systems disclosed herein allow for the production of one or more usable, potentially economically valuable products from MSW diverted to the MSWP system from a landfill. Also disclosed herein, additionally, are embodiments of systems and methods for generating one or more carbon credits by processing the MSW diverted to the MSWP system.

Figure 1:
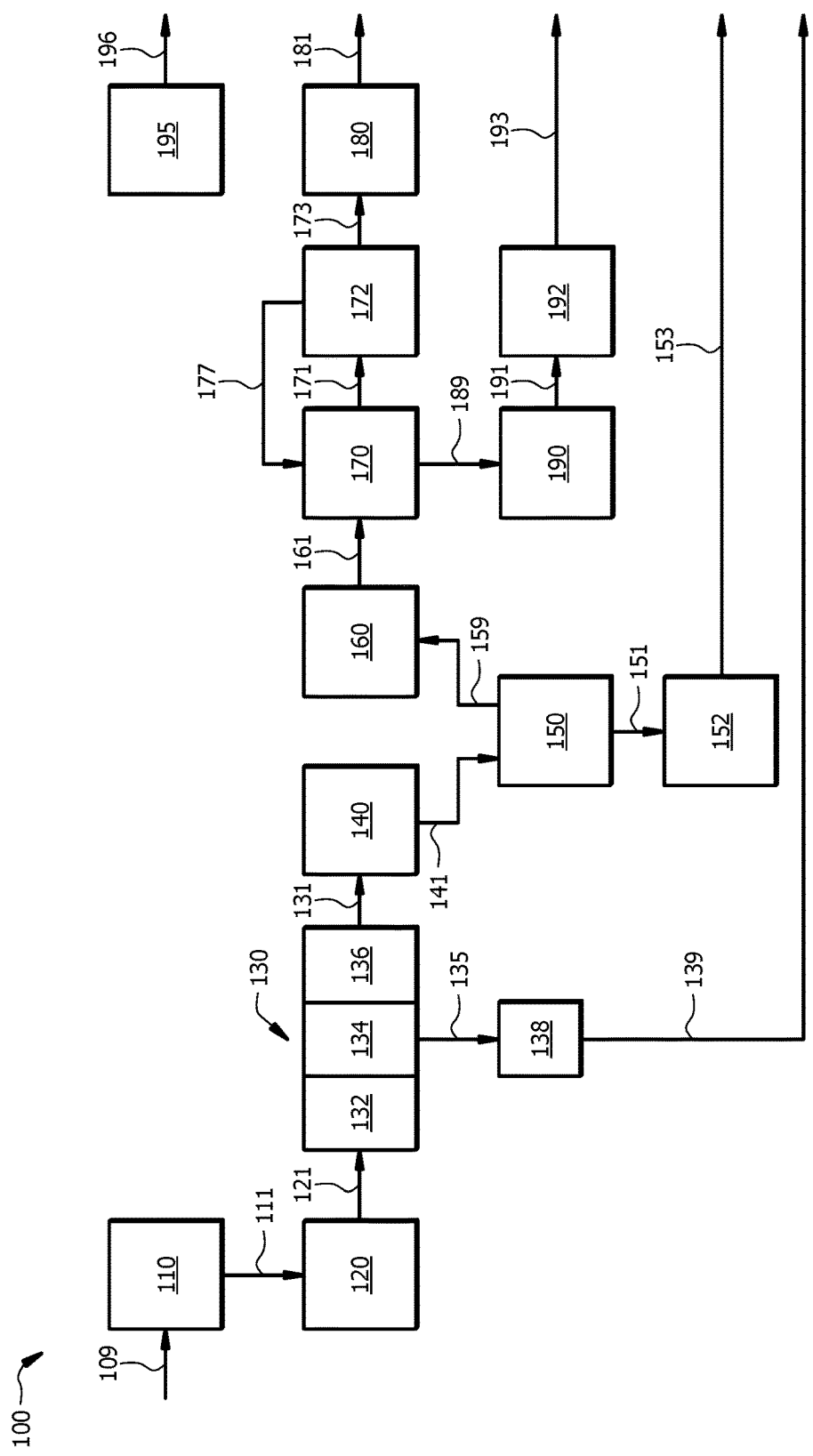
FIG. 1 illustrates a MSW processing system according to a first embodiment disclosed herein.

Referring to FIG. 1, an embodiment of a MSWP system 100 is illustrated. In the embodiment of FIG. 1, the MSWP system 100 is particularly configured for and/or employed in a process for receiving an intake of MSW 109 (e.g., MSW in a given mass, volume, tonnage, etc.), for example, that has been diverted to the MSWP from a landfill or other conventional MSW disposal site (e.g., an incinerator, etc.) and for producing one or more salable, alcohol product streams 181, a compressed carbon dioxide stream 193, a hydrogen gas stream 153, and a biochar output 139.

The MSWP system 100 of FIG. 1 generally comprises a MSW processor unit 110, a Refuse-Derived Fuel (RDF) unit 120, a gasification system 130, an ash system 138, a syngas compressor 140, a hydrogen membrane 150, a pressure swing absorption (PSA) unit 152, a contaminant removal unit 160, a mixed alcohol synthesis unit 170, an alcohol separation unit 172, an alcohol storage unit 180, a carbon dioxide removal unit 190, a carbon dioxide compressor 192, and a steam turbine 195. These various MSWP systems, units, and components are in fluid communication via appropriate conduits, piping, valves, etc., for example, as shown in the various figures and described in more detail herein.

In the embodiment of FIG. 1, the MSW processor unit 110 is generally configured to receive the MSW 109 and to convert the MSW 109 to a form usable in the processes disclosed herein (e.g., a form suitable for gasification, as will be disclosed herein). In an embodiment, the MSW 109 received at or via the MSW processor unit 110 is quantified upon intake (for example, the MSW 109 is received in a known, given mass, volume, tonnage, etc. or is otherwise measured, e.g., weighted via scales). In an embodiment, the MSW 109 may be characterized as having a moisture content of from about 20% to about 60%, by weight, alternatively, from about 30% to about 50%, alternatively, of about 40%. The composition of the MSW 109 may vary dependent upon factors including the municipality and/or region from which the MSW 109 is received and whether the MSW 109 has been subject to any prior separation or sorting process. In an embodiment, the MSW 109 comprises one or more carbonaceous materials. More particularly, the MSW 109 comprises various carbonaceous and non-carbonaceous materials including, but is not limited to, biodegradable waste, such as food and kitchen waste, green waste, and paper; recyclable materials, such as paper, cardboard, glass, metals (e.g., aluminum), plastics, clothes, tires, and batteries; inert waste, such as construction and demolition debris, dirt, and rocks; electronic waste, such as electrical appliances, computers, and televisions; composite materials such as clothing, Tetra Packs, plastics (e.g., products having multiple types of plastics); hazardous waste, such as paint, chemicals, light bulbs, spray cans, fertilizers, pesticides, herbicides, and fungicides; and medical waste. In an embodiment, the MSW 109 may be pre-sorted, for example, to remove waste that could be hazardous if subjected to the processing herein disclosed.

In an embodiment, the MSW processor unit 110 is configured to separate a usable portion of the MSW 109 (e.g., carbonaceous materials, such as paper, food waste, or plastics) from an unusable portion thereof (e.g., non-carbonaceous or inert materials, such as glass, metals, rocks, dirt, etc.). For example, the MSW processor may comprise a magnetic separator, a density-based separator (e.g., an "air knife"), a cyclonic separator, the like, or combinations thereof.

The MSW processor unit 110 may be further configured to shred, pulverize, grind, dry, dehydrate, sterilize, size, screen, and/or otherwise process the MSW 109 or a portion thereof (e.g., a portion of the MSW 109 remaining after separating usable and unusable components). In the embodiment of FIG. 1, the MSW processor unit 110 produces and outputs a RDF 111. The RDF 111 may comprise pellets, bricks, or logs comprising organic material, for example, at least 50% by weight or organic material, alternatively, at least 60%, alternatively, at least 70%, alternatively, at least 80%, alternatively, at least 90%, alternatively, at least 95% organic materials. In an embodiment, the RDF 111 may be dehydrated, for example, such that the RDF 111 has a moisture content of less than about 20% by weight, alternatively, less than 15%, alternatively, less than 12.5%, alternatively, less than 10%, alternatively, less than 7.5%, alternatively, less than 5%, alternatively, less than 2.5%, alternatively, less than 1%. In an alternative embodiment, the RDF 111 is not dehydrated, for example, such that the RDF 111 has a moisture content of from about 20% to about 60%, by weight, alternatively, from about 30% to about 50%, alternatively, of about 40%.

Referring again to the embodiment of FIG. 1, the RDF 111 (e.g., carbonaceous materials) are, optionally, routed to the RDF unit 120 where the RDF 111 can be stored until ready for use.

In the embodiment of FIG. 1, the RDF 121 is fed into gasification system 130, which is generally configured to receive the RDF 121 and, optionally, additional media such as grey water and recycled condensate, and air. Generally speaking, the gasification system 130 is configured to utilize heat, pressure, and the injected water/steam to drive the following chemical reaction to yield carbon monoxide (CO) and gaseous hydrogen($H_2$):

$$C+H_2O=CO+H_2.$$

In the embodiment of FIG. 1, the gasification system 130 is illustrated as comprising a pyrolysis unit 132, a gasification reactor 134, and a scrubber 136. An example of a suitable, commercially-available gasification system is made available by TCG Global. Examples of suitable gasification systems are also disclosed in U.S. Pat. Nos. 7,638,070; 1,857,995; 7,968,006; 8,017,040; 8,017,041; 8,021,577; and 8,197,698, each of which is incorporated by reference herein in its entirety. In alternative embodiments, other suitable configurations of gasification systems may be used.

In the embodiment of FIG. 1, the RDF 121 is fed into the pyrolysis unit 132 of the gasification system 130. The pyrolysis unit 132 is generally configured to thermally decompose the RDF at a temperature range of from 390 to about 570 CF (200-300° C.) in the absence of oxygen, thereby driving off moisture and volatile gases contained in the feedstock. Pyrolysis in the pyrolysis unit produces carbon char and ash which are conveyed into the gasification reactor 134. The gasification reactor 134 is externally heated to an internal temperature of at least about 1300° F. (700° C.). In the gasification reactor 134, solid carbon is volatilized to a gaseous state and water (e.g., ionized water and/or steam) is injected (e.g., steam reformation) to shift the reaction toward the production of carbon monoxide and hydrogen gas (e.g., shift to the right, in the chemical reaction shown above), thereby producing synthesis gas ("syngas"). Notably, while conventional gasification plants produce high amounts of carbon dioxide as a result of internal combustion processes, an externally heated process may yield a reduction in the production of carbon dioxide. Tu an embodiment, the gasification is carried out in the substantial absence, alternatively in the absence of, internal combustion of the carbon containing feedstock material (i.e., no feedstock combustion within the gasification chamber), and likewise in the absence or substantial absence of internal combustion byproducts (e.g., minimal or no $CO_2$ production and related emissions) Additionally, in an embodiment, the syngas is water quenched and cleansed of its impurities in the scrubber 136, yielding a scrubbed syngas. In an embodiment, the scrubbed syngas 131 may comprise, for example, $H_2$, CO, $CO_2$, $CH_4$, $H_2O$, heavy hydrocarbons, and oxygenated compounds. In various embodiments, the composition of the syngas may vary based upon the composition of the MSW 109 input into the disclosed MSWP system 100.

Referring again to FIG. 1, the carbon char and ash produced via the gasification system 130 (e.g., in the gasification reactor 134) are output as a waste stream 135 to the ash system 138. The ash and carbon char may be further processed, for example, including separation processes, sizing (e.g., powdering, etc.), and the like, in the ash system 138 to yield a biochar output 139. Biochar is a charcoal-like, carbon-containing mass that may be useful as a soil amendment (e.g., to improve soil fertility and/or to improve water retention with a soil) or as a carbon sink. The biochar output thus comprises an economically-valuable product from the disclosed systems and processes.

Referring again to FIG. 1, the scrubbed syngas 131 may be compressed in the syngas compressor 140, for example, to a suitable pressure for further processing. In an embodiment, the compressed syngas stream 141 may have a pressure of from about 3000 psi to about 3200 psi, alternatively, from about 1500 psi to about 1600 psi, alternatively, from about 1700 psi to about 1800 psi.

In the embodiment of FIG. 1, the compressed syngas stream 141 is routed to the hydrogen membrane 150 which is generally configured to separate at least a portion of the hydrogen gas within the compressed syngas stream 141 from any additional gaseous components (e.g., CO, $CO_2$, $CH_4$, $H_2O$, heavy hydrocarbons, and oxygenated compounds). The hydrogen membrane 150 is generally configured to permit transport (e.g., passing through the membrane) of hydrogen gas while limiting transport of another gas. As will be appreciated by one of skill in the art upon viewing this disclosure, gaseous mixture may be separated via the use of various synthetic membranes, examples of which include polymer membranes, such as polyamide or cellulose acetate, or from ceramic membranes. In an embodiment, the hydrogen membrane 150 is a palladium membrane or a palladium-silver alloy membrane generally configured to solely permit transport of hydrogen gas. The hydrogen membrane may be configured to reduce the proportion or concentration of hydrogen gas within the syngas. For example, in an embodiment, the compressed syngas stream 141 (e.g., pre-separation via the hydrogen membrane 150) may be characterized as having a $H_2$/CO ratio of about 1.5 while a hydrogen-lean syngas stream 159 (e.g., post-separation via the hydrogen membrane 150) may be characterized as having a $H_2$/CO ratio of about 1.1. The hydrogen membrane, thus, yields the hydrogen-lean syngas stream 159 and a hydrogen gas enriched stream 151.

Referring again to FIG. 1, the hydrogen gas enriched stream 151 is introduced into the PSA unit 152 to produce a hydrogen gas stream 153 and a PSA off-gas that may comprise, for example, methane and/or carbon dioxide. In an embodiment, the PSA unit 152 comprises an adsorbent material. PSA is generally based on physical binding of gas molecules (e.g., hydrogen, methane, carbon dioxide, etc.) to an adsorbent material. Binding strength between the gas molecules and the adsorbent material depends on the gas components, type of adsorbent material, partial pressures of the gas components and operating temperature. Purifying a gas by PSA separation is based on differences in binding strength of the gas components to the adsorbent material. Highly volatile components with low polarity, such as hydrogen, are practically non-adsorbable, as opposed to molecules like methane and carbon dioxide. PSA generally includes an adsorption step and a desorption step. During the adsorption step, high purity hydrogen can be recovered from a PSA unit, as hydrogen will not be adsorbed, Methane and carbon dioxide will be adsorbed by the adsorbent material, and can be recovered during the desorption step.

PSA works at basically constant temperature and uses the effect of alternating pressure and partial pressure to yield the adsorption and the desorption steps. The adsorption may be carried out at high pressure, until an equilibrium loading is reached and no further adsorption capacity is available; thus, the adsorbent material must be regenerated. The regeneration step may be carried out by lowering the pressure to slightly above atmospheric pressure resulting in a respective decrease in equilibrium loading. As a result, the gases (e.g., methane, carbon dioxide) that were adsorbed by the adsorbent material are desorbed and the adsorbent material is regenerated. Once the regeneration step is completed, the pressure is increased back to adsorption pressure level and another adsorption step begins. Generally, PSA also involves a purge step between the desorption step and the adsorption step, to ensure that the adsorber material is ready to undergo the next adsorption step. Non-limiting examples of adsorbent materials suitable for use in the PSA unit 152 include molecular sieves, zeolites, such as 5A zeolite and 13X zeolite, and the like., or combinations thereof.

In an embodiment, the hydrogen gas stream 153 may be characterized by a purity of equal to or greater than about 99%, alternatively equal to or greater than about 99.9%, or alternatively equal to or greater than about 99.99%. In an embodiment, the hydrogen gas stream 153 yields a salable product, for example, that may be used in various industrial processes or by consumers (e.g., in a hydrogen fuel-cell vehicle).

Referring again to the embodiment of FIG. 1, the hydrogen-lean syngas stream 159 is routed to the contaminant removal unit 160. In various embodiments, the contaminant removal unit 160 is generally configured to remove at least a portion of contaminants such as sulfur-containing compounds and chlorides from the hydrogen-lean syngas stream 159, thereby yielding a decontaminated syngas stream 161.

In the embodiment of FIG. 1, the decontaminated syngas stream 161 is fed into the alcohol synthesis unit 170. In alternative embodiments, the scrubbed syngas stream 131 (or compressed syngas stream 141) could be fed directly into the alcohol synthesis unit 170, for example, depending upon the composition of the syngas produced by the gasification system 130. In an embodiment, the syngas fed into the alcohol synthesis unit 170 is characterized as having a $H_2/CO$ ratio of from about 1.0 to about 1.2, alternatively, of about 1.1. In an embodiment, a Syngas having a $H_2/CO$ ratio of from about 1.0 to about 1.2, alternatively, of about 1.1, may exhibit improved production of alcohols in the alcohol synthesis unit 170. In the alcohol synthesis unit, CO and $H_2$ are reacted, in a series of concurrently-occurring reactions, to yield methanol, ethanol, propanol, butanol, alkanes, esters, ethers, or combinations thereof.

The alcohol synthesis unit 170 can utilize any commercially suitable catalysts, and the specific catalyst used will depend on the composition of the syngas feed, as well as the desired composition of a mixed alcohols stream 171 produced by the alcohol synthesis unit 170. In an embodiment, the catalyst is molybdenum sulfide and, in such an embodiment, the syngas fed into the alcohol synthesis unit 170 is characterized as comprising from about 50 to about 100 ppm sulfur containing compounds, for example, as may be dependent upon the catalyst(s) employed therein. The alcohol synthesis unit 170 is configured to produce the mixed alcohols stream 171 and a carbon dioxide off-gas stream 189. In an embodiment, the composition of the mixed alcohols stream 171 may vary based upon the composition of the MSW 109 that is utilized and/or upon the particular configuration of MSWP system that is employed. For example, in various embodiments, the mixed alcohol stream may comprise from about 0 to about 30 vol. % methanol, from about 25 to about 70 vol. % ethanol, from about 5 to about 20 vol. % propanol, from about 0 to about 5 vol. % butanol, and from about 0 to about 1 vol. % pentanol and heavier alcohols.

Referring again to FIG. 1, the mixed alcohols stream 171 may be fed into the alcohol separation unit 172, which is configured to receive at least a portion of the mixed alcohols stream 171 and, generally, to produce two or more streams each substantially comprising an alcohol having a desired carbon-number or range of carbon-numbers. In various embodiments, the alcohol separation unit 172 may be configured as a column (e.g., a fractionating or distillation column). For example, in the embodiment of FIG. 1, the alcohol separation unit 172 is generally configured to separate methanol from ethanol and higher carbon-number alcohols. In an embodiment, at least some of a methanol stream is fed back to the alcohol synthesis unit 170 as a recycle stream 177, for example, directly to alcohol synthesis unit 170 or mixed into the compressed syngas stream 141 or the scrubbed syngas stream 131 upstream of the alcohol synthesis unit 170. In such an embodiment, the methanol (e.g., which may be less desirable) may be recycled to minimize the amount of methanol produced while increasing the production of higher carbon-number alcohols (e.g., when compared with a single pass development lacking such a methanol recycling stream). In an embodiment, such a recycle stream 177 may comprise less than about 20 vol. % ethanol and higher carbon-number ($C_{2+}$) alcohols, alternatively, less than about 10%, alternatively, less than about 5%. The alcohol separation unit 172 also outputs a product stream 173, for example, comprising ethanol, propanol, butanol, propanol, and higher carbon-number alcohols. In various embodiments, the product stream 173 may comprise about 50 to about 75 vol. ethanol, from about 10 to about 40 vol. % propanol, from about 0 to about 10 vol. % butanol, and from about 0 to about 5 vol. % pentanol and heavier alcohols. In an embodiment, the product stream 173 is substantially depleted of methanol (e.g., methanol free or substantially methanol free). For example, in an embodiment, the product stream 173 comprises less than 5 vol. % methanol, alternatively, less than 2.5% methanol, alternatively, less than 1% methanol. In additional embodiments, the product stream 173 may be further separated into two or more streams, each stream comprising two or more of ethanol, propanol, butanol, propanol, and higher carbon-number alcohols.

In the embodiment of FIG. 1, the product stream 173 is routed from the alcohol separation unit 172 to the alcohol storage unit 180 for storage, blending, polishing, denaturing, etc. and subsequent sale. Thus, accordingly, one or more salable, alcohol product streams 181 may be provided, for example, that may be used in various industrial processes.

Referring again to FIG. 1, the carbon dioxide off-gas stream 189 from the alcohol synthesis unit 170 is routed to the carbon dioxide removal unit 190. The carbon dioxide removal unit 190 is generally configured to selectively remove carbon dioxide from a gaseous stream. An example of a suitable configuration for the carbon dioxide removal unit 190 is the Fluor Solvent Process developed by Fluor™ Corp., although any commercially-available, suitable process may be similarly employed. The carbon dioxide removal unit 190 yields a carbon dioxide stream 191 comprising substantially pure carbon dioxide. For example, the carbon dioxide stream 191 may comprise at least 95 vol. % of carbon dioxide, alternatively, at least 98%, alternatively, at least 99%, alternatively, at least 99.5%.

In the embodiment of FIG. 1, the carbon dioxide stream 191 is routed to the carbon dioxide compressor 192 for compression, for example, such that carbon dioxide may be stored or made available for sale in a compressed, gaseous state. The carbon dioxide compressor yields a compressed carbon dioxide stream 193. In various embodiments, the compressed carbon dioxide stream 193 may have any suitable pressure, for example, from about 10 to about 150 psi, alternatively, from about 75 to about 125 psi. The compressed carbon dioxide stream 193 constitutes a salable product, for example, for use in carbonation processes (e.g., by food and beverage producers), for use by consumers, or in various industrial processes.

In the embodiment of FIG. 1, excess steam and/or heat (e.g., which may be converted to steam) output from one or more components of the MSWP system 100 are routed to a turbine generator, e.g., steam turbine 195, which is configured to generate electricity from excess/discarded process steam (e.g., cogeneration), for example, by converting the thermal energy from pressurized steam into rotational energy to thereby drive an electric generator. In such an embodiment, the electricity generated via the steam turbine 195 may be used to power one or more components of the MS WP system 100 (e.g., compressors, separators, pumps, etc.). Waste steam/condensate is typically recovered from the turbine, for example, via stream 196. As such, the steam turbine 195 may improve the overall efficiency of the MSWP system 100 by decreasing the inputs (e.g., power) necessary for the MSWP system 100 to operate.

Figure 2:
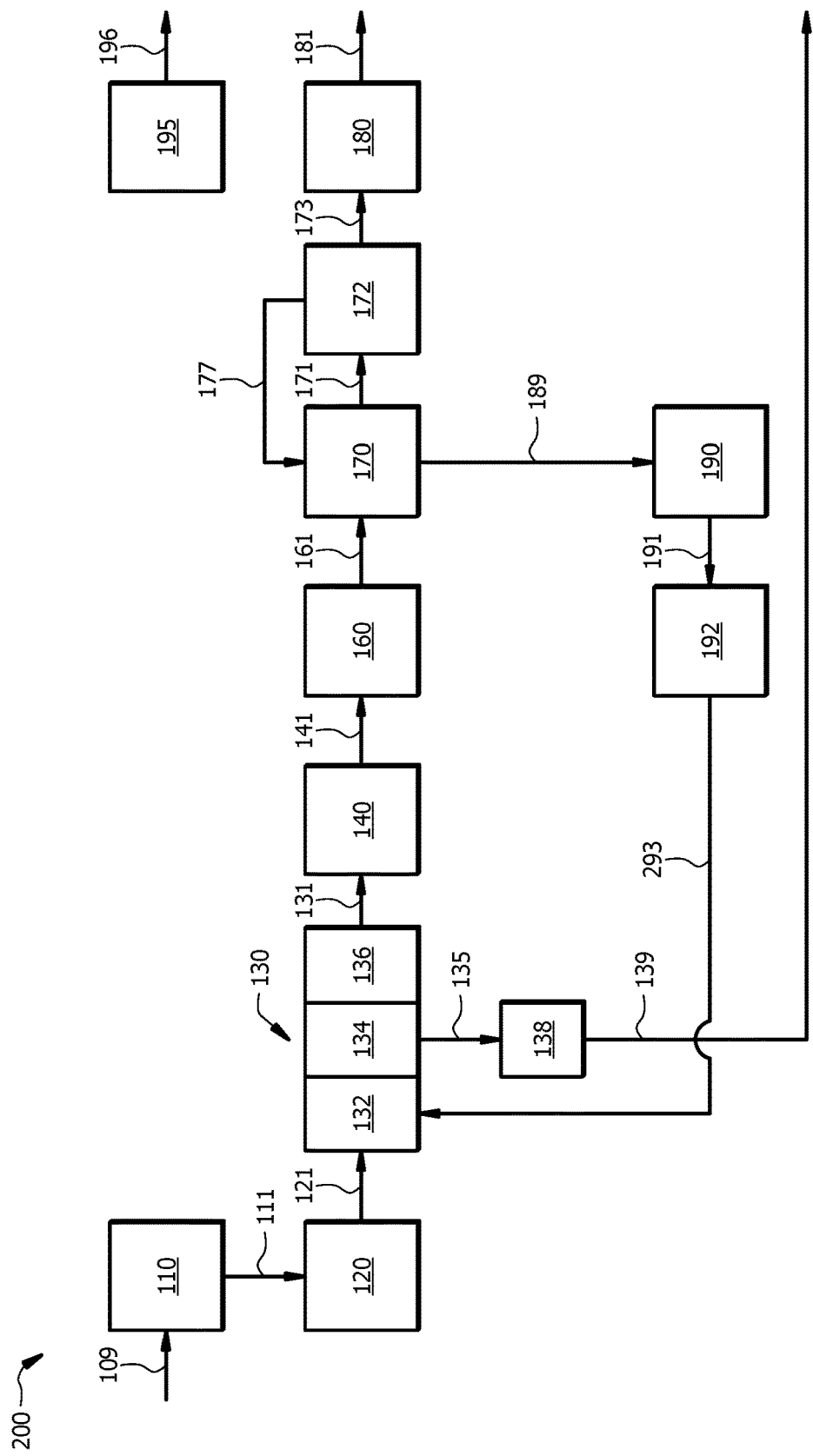
FIG. 2 illustrates a MSW processing system according to a second embodiment disclosed herein.

Referring to FIG. 2, an alternative embodiment of a MSWP system 200 is illustrated. In the embodiment of FIG. 2, the MSWP system 200 is particularly configured, as similarly disclosed with respect to FIG. 1, for receiving the intake of MSW 109 (e.g., MSW in a given mass, volume, tonnage, etc.), for example, that has been diverted to the MSWP from a landfill or other conventional MSW disposal site (e.g., an incinerator, etc.) and, as also disclosed with respect to FIG. 1, for producing the one or more salable, alcohol product streams 181 and the biochar output 139. The MSWP system 200 comprises the same components as disclosed with respect to FIG. 1 (and numbered correspondingly), those components being configured to operate as disclosed with respect to FIG. 1, with the exceptions noted below.

First, in the embodiment of FIG. 2, the MSWP system 200 lacks the hydrogen membrane 150 and pressure swing absorption (PSA) unit 152. Rather, in the embodiment of FIG. 2, the compressed syngas stream 141 is routed directly to the contaminant removal unit 160.

Second, in the embodiment of FIG. 2, a compressed carbon dioxide stream 293 from the carbon dioxide compressor 192 is returned to the gasification. System 130 and is input into the pyrolysis unit 132. In the embodiment of FIG. 2, returning the compressed carbon dioxide stream 293 to the pyrolysis unit 132 may be effective to alter the $H_2/CO$ ratio of the syngas produced via the gasification system 130 (e.g., by yielding a relative increase in the amount of carbon monoxide). As previously noted, a $H_2/CO$ ratio of about 1.1 may be beneficial to the production of alcohols in the alcohol synthesis unit 170. Additionally, returning the compressed carbon dioxide stream 293 to the pyrolysis unit 132 may also be effective to increase the yield of carbon monoxide produced and, thus, increasing the yield of mixed alcohols produced via the operation of the MSWP system 200.

Figure 3:
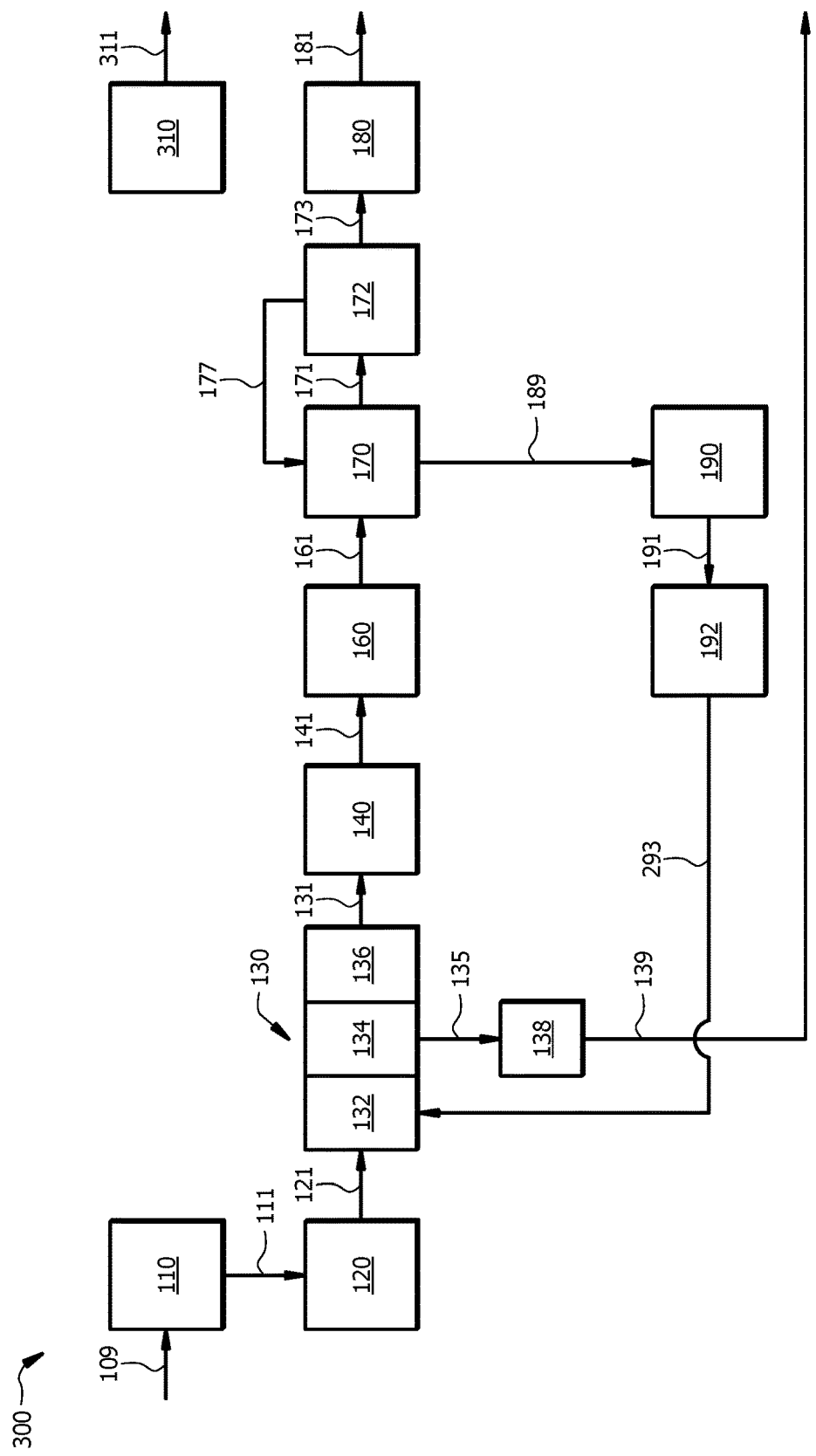
FIG. 3 illustrates a MSW processing system according to a third embodiment disclosed herein.

Referring to FIG. 3, another alternative embodiment of a MSWP system 300 is illustrated. In the embodiment of FIG. 3, the MSWP system 300 is particularly configured, as similarly disclosed with respect to FIG. 2, for receiving the intake of MSW 109 (e.g., MSW in a given mass, volume, tonnage, etc.), for example, that has been diverted to the MSWP from a landfill or other conventional MSW disposal site (e.g., an incinerator, etc.) and, as also disclosed with respect to FIG. 2, for producing the one or more salable, alcohol product streams 181 and the biochar output 139. The MSWP system 300 comprises the same components as disclosed with respect to FIG. 2 (and numbered correspondingly), those components being configured to operate as disclosed with respect to FIG. 2, with the exception that, in the embodiment of FIG. 3, the MSWP system 300 lacks the turbine generator 195 utilized to generate power to operate the MSWP system 200.

Rather, in the embodiment of FIG. 3, the steam employed to power a turbine generator steam turbine 195 of FIGS. 1 and 2) is instead routed to an off-site power generation unit, for example, a conventionally-fired power plant, such as a coal-fired power plant having one or more turbines 310. Waste steam/condensate is typically recovered from the turbine 310, for example via stream 311. For example, in an embodiment where the MSWP system 300 is physically located in relatively close proximity to such a conventional power plant, the steam generated in the operation of the MSWP system 300 may be routed to the conventional power plant, for example, to supplement the steam generated at such conventional power plant by conventional means (e.g., burning fossil fuels, such as coal). Additionally, in an embodiment, steam generated in the operation of the MSWP system 300 may be routed to other proximately-located industrial facilities requiring heat (e.g., steam) for the processes there-performed. As such, there may be an additional advantage to locating a MSWP system like MSWP system 300 proximate to another industrial facility.

Figure 4:
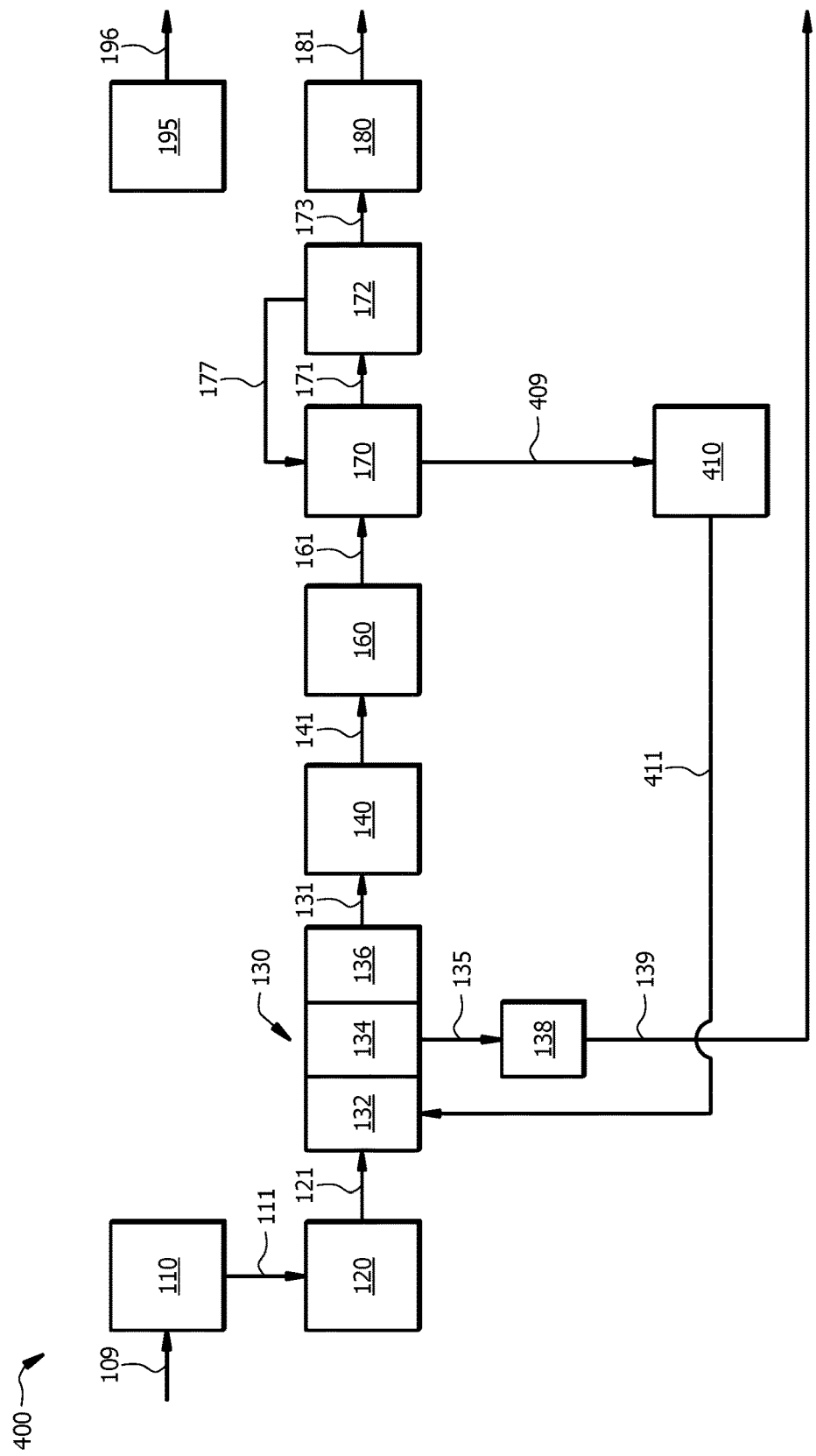
FIG. 4 illustrates a MSW processing system according to a fourth embodiment disclosed herein.

Referring to FIG. 4, another alternative embodiment of a MSWP system 400 is illustrated. In the embodiment of FIG. 4, the MSWP system 400 is particularly configured, as similarly disclosed with respect to FIG. 2, for receiving the intake of MSW 109 (e.g., MSW in a given mass, volume, tonnage, etc.), for example, that has been diverted to the MSWP from a landfill or other conventional MSW disposal site (e.g., an incinerator, etc.) and, as also disclosed with respect to FIG. 2, for producing the one or more salable alcohol product streams 181 and the biochar output 139. The MSWP system 400 comprises the same components as disclosed with respect to FIG. 2 (and numbered correspondingly), those components being configured to operate as disclosed with respect to FIG. 2, with the exception that, in the embodiment of FIG. 4, the MSWP system 400 lacks the carbon dioxide removal unit 190 and carbon dioxide compressor 192 and, instead, the MSWP system 400 of FIG. 4 comprises a recycle gas compressor 410.

In the embodiment of FIG. 4, a recycle gas stream 409 from the mixed alcohol synthesis unit 170 is compressed via the operation of the recycle gas compressor 410 returned to the pyrolysis unit 132 as a compressed recycle gas stream 411. In the embodiment of FIG. 4, the introduction of the compressed recycle gas stream 411 into the pyrolysis unit 132 may also be effective to increase the yield of carbon monoxide produced and, thus, increasing the yield of mixed alcohols produced via the operation of the MSWP system 40.

Figure 5:
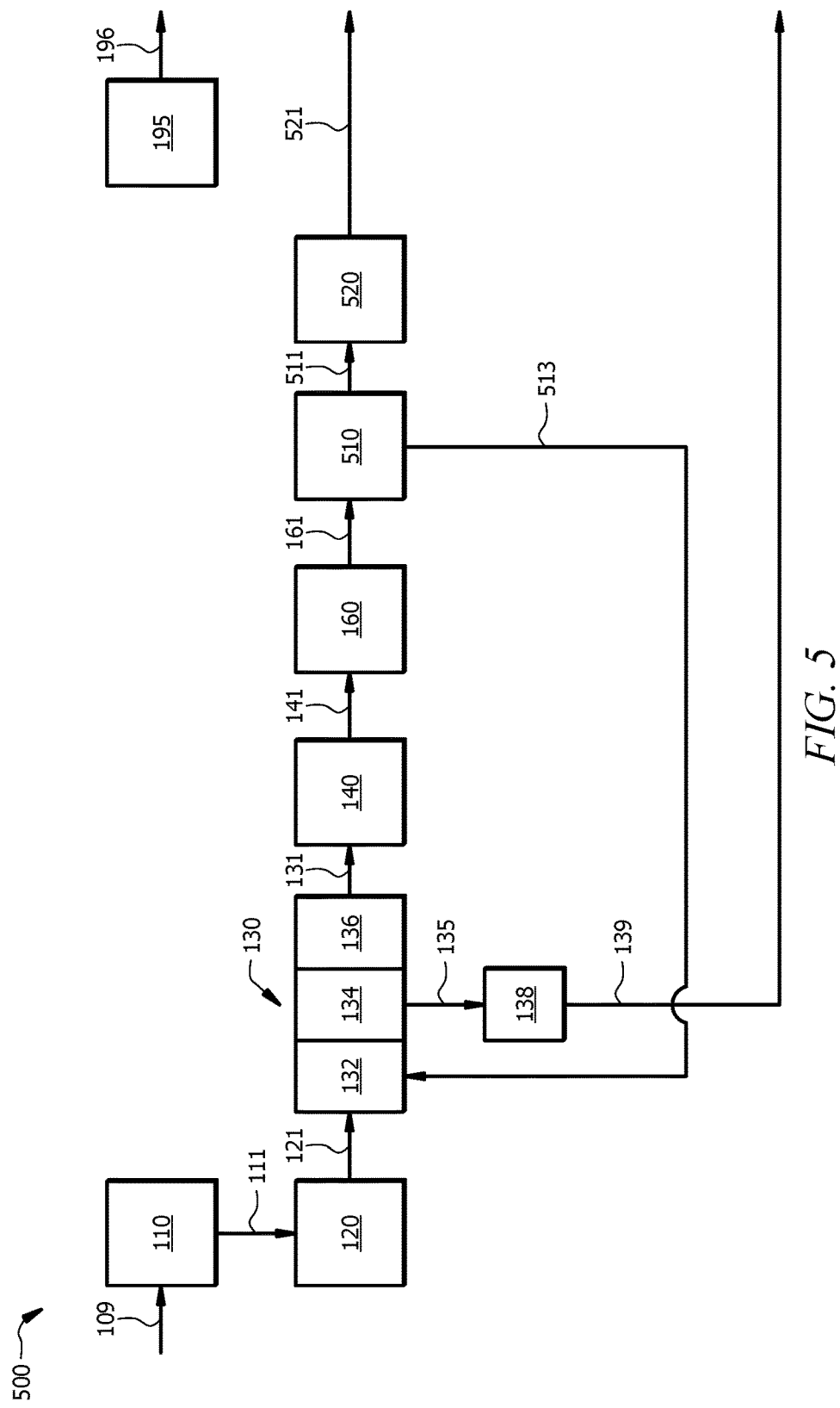
FIG. 5 illustrates a MSW processing system according to a fifth embodiment disclosed herein.

Referring to FIG. 5, another alternative embodiment of a MSWP system 500 is illustrated. In the embodiment of FIG. 5, the MSWP system 500 is particularly configured, as similarly disclosed with respect to FIG. 2, for receiving the intake of MSW 109 (e.g., MSW in a given mass, volume, tonnage, etc.), for example, that has been diverted to the MSWP from a landfill or other conventional MSW disposal site (e.g., an incinerator, etc.). In the embodiment of FIG. 5, the MSWP system 500 is configured for producing biochar output 139 and, additionally, fuel product stream 521. The MSWP system 500 comprises the same components as disclosed with respect to FIG. 2, those components being configured to operate as disclosed with respect to FIG. 2 (and numbered correspondingly), with the exception that, in the embodiment of FIG. 5, the MSWP system 500 lacks the mixed alcohol synthesis unit 170, the alcohol separation unit 172, the alcohol storage unit 180, the carbon dioxide removal unit 190, and the carbon dioxide compressor 192.

Instead, the MSWP system 500 of FIG. 5 comprises a Fischer-Tropsch (FT) unit 510 and a hydrocracker 520. The FT unit 510 is generally configured to convert a syngas stream (e.g., one or more of scrubbed syngas stream 131, compressed syngas stream 141, and decontaminated syngas stream 161) to a FT product stream 511 comprising FT liquids and FT wax.

In the embodiment of FIG. 5, the decontaminated syngas stream 161 can be converted to liquid hydrocarbons (e.g., FT hydrocarbon liquids) via the FT process. The FT process generally comprises a catalyzed chemical reaction in which carbon monoxide and hydrogen in the syngas are converted into hydrocarbons of various molecular weights according to the general reaction, $(2n+1) H_2 + n CO \rightarrow C_nH_{(2n+2)} + n H_2O$ (e.g., the FT reaction), wherein n is an integer. There are other side reactions taking place in the FT process, including a water-gas shift (WGS) reaction, $CO + H_2O \rightleftharpoons H_2 + CO_2$. FT process conditions can be selected to achieve a desired hydrocarbon product distribution. For example, catalyst, temperature, and type of process may be varied, as will be appreciated by one of skill in the art upon viewing this disclosure, to produce a mixture of hydrocarbons ranging in composition from methane to higher molecular weight paraffins, aromatic hydrocarbons, and olefins; as well as small amounts of low molecular weight oxygenates (e.g., alcohol and organic acids). Waxes (e.g., FT waxes comprising longer-chain paraffins with 20 to 40 carbon molecules that are solid at standard conditions) can also be formed in an FT process. In such an embodiment, such waxes can be cracked to shorter, liquid forms, for example, via the hydrocracker 520.

In an embodiment, the FT product comprises a tail gas, unconverted syngas, distillate, light hydrocarbons, naphtha, jet fuel, diesel waxes, or combinations thereof. In an embodiment, the FT product comprises FT wax in an amount of less than about 30 wt. %, alternatively less than about 40 wt. %, or alternatively less than about 50 wt. %, with the balance of the Fir product being non-waxy liquid hydrocarbons (e.g., FT hydrocarbon liquids).

In an embodiment, the FL unit 510 can comprise any suitable type or configuration of FI reactor, such as for example a tubular reactor, a multitubular reactor, a fixed bed reactor, a multitubular fixed-bed reactor, a fluidized bed reactor, a slurry reactor, micro-channel reactor, and the like, or combinations thereof. The FT reaction is highly exothermic, therefore efficient heat removal is an important feature of the unit 510 (e.g., a reactor). In an embodiment, the FT unit 510 can comprise an FT catalyst, examples of which include, but are not limited to, transition metals, such as iron, cobalt, nickel, ruthenium, etc. The FT reaction temperature can be generally controlled by cooling the reactor to achieve the desired FT reaction temperature, for example by using a cooling liquid such as water.

In the embodiment of FIG. 5, the FT unit 510 also yields an FT tail gas stream 513. The FT tail gas stream 513 can comprise olefins, unreacted syngas (including carbon monoxide and hydrogen), and carbon dioxide. Additionally, fuel gases like methane, propane, and butane may also be present as part of the FT tail gas stream 513. The FT tail gas stream 513 may be fed back to the gasification system 130, for example to the pyrolysis unit 132 wherein the contents of the FT tail gas stream may undergo further pyrolysis and gasification.

In the embodiment of FIG. 5, the FT product stream 511 (e.g., comprising FT hydrocarbons liquid and FT wax s introduced into the hydrocracker 520 (e.g., hydrocracking unit), for example, to produce an additional volume of liquid hydrocarbons. In alternative embodiments, the FT wax can be separated from the FT product stream 511 and the FT wax introduced to the hydrocracker for processing. Generally, the hydrocracker 520 is configured to crack or split heavy molecules into smaller or lighter molecules in the presence of hydrogen and a catalyst. There are two main chemical reactions occurring in the hydrocracker: (i) catalytic cracking of heavy hydrocarbons into lighter unsaturated hydrocarbons and (ii) saturation of these newly formed hydrocarbons with hydrogen. Catalytic cracking of the heavier hydrocarbons uses heat and causes the feed to be cooled as it progresses through the hydrocracker. The saturation of the lighter hydrocarbons releases heat and causes the feed and products to heat up as they proceed through the hydrocracker. Hydrogen can be used to control the temperature of the hydrocracker, by introducing the hydrogen to the hydrocracker at different points. In an embodiment, at least a portion of the hydrogen recovered from the MSWP system 500 (e.g., from the PSA unit 152, as disclosed with respect to FIG. 2, which may similarly be included in the embodiment of FIG. 5) can be introduced to the hydrocracker. In various embodiments, the hydrocracker 520 may comprise a bifunctional catalyst that is capable of rearranging and breaking hydrocarbon chains as well as adding hydrogen to aromatics and olefins to produce naphthenes and alkanes, respectively. In some embodiments, a hydrocracking catalyst can comprise both acidic sites, which provide the cracking function, and metal sites, which provide the hydrogenation-dehydrogenation function. Typical acidic supports for hydrocracking catalysts can be amorphous oxides or mixtures of oxides, zeolites, and silicoalumina-phosphates. Pt, Pd, and/or bimetallic systems (e.g., Ni/Mo, Ni/W, Co/Mo, in the sulfided form) are the most commonly used metals for hydrocracking catalysts.

In the embodiment of FIG. 5, the hydrocracker 520 yields a fuel product stream 521, for example, comprising diesel fuel, jet fuel, gasoline, and the like, or combinations thereof.

The fuel product stream 521 can be separated into two or more fractions, for example, via distillation. In an embodiment, the fuel can comprise various liquid hydrocarbons collected as different fractions, such as a jet fuel fraction, a diesel fuel fraction, a gasoline fraction, a naphtha fraction, etc. In such an embodiment, the naphtha fraction may be introduced to a naphtha reformer to produce a high-octane fuel and hydrogen. The fuel product stream 521 may optionally undergo further storage or processing such as that described in alcohol storage unit 180.

Each of the embodiments of FIGS. 1, 2, 3, 4, and 5 illustrate various embodiments of MSWP systems for production of one or more usable, potentially economically valuable products from MSW diverted from a landfill to a MSWP system like one or more of MSWP systems 100, 200, 300, 400, or 500. Additionally or alternatively, it is recognized that aspects or elements of two or more alternative configurations of a MSWP system (aspects or elements from two or more of MSWP systems 100, 200, 300, 400, and 500) may be combined in a MSWP configuration not specifically disclosed or illustrated, but nonetheless contemplated and appreciated by one of skill in the art upon viewing the instant disclosure.

In an embodiment, a MSWP system (e.g., one or more of MSWP systems 100, 200, 300, 400, or 500) as disclosed herein for diverting MSW from a landfill may also be configured for and/or employed in a process for generating a carbon credit. Further to one or more of the steps described above with respect to the embodiments of a method of diverting MSW from a landfill, generating a carbon credit may further comprise the step of quantifying a reduction in emissions of carbon dioxide or a GHG having a carbon dioxide equivalency and the step of claiming the carbon credit associated with the reduction in emissions of carbon dioxide or the GHG having the carbon dioxide equivalency (e.g., a carbon offset).

Every GHG has a global warming potential ("GWP"), a measurement of the impact that particular gas has on "radiative forcing"; that is, the additional heat/energy which is retained in the Earth's ecosystem as a result of the addition of this particular gas to the atmosphere. The GWP of a given gas describes its effect on climate change relative to a similar amount of carbon dioxide. As the base unit, carbon dioxide's GWP numeric is 1.0. This allows regulated GHGs to be converted to the common unit of carbon dioxide equivalents ("$CO_2e$"). For example, methane, a $CO_2e$, has a GWP of 25—meaning that one ton of methane will have an effect on global warming that is 25 times greater than one ton of carbon dioxide.

Carbon trading (e.g., trading carbon credits) is an application of an emissions trading scheme. GHG emissions are capped and then markets are used to allocate the emissions among the group of regulated sources. The goal is to allow market mechanisms to drive industrial and commercial processes in the direction of low emissions or less carbon intensive approaches than those used when there is no cost to emitting carbon dioxide and other GHGs into the atmosphere. Since GHG reduction projects generate credits (e.g., associated with carbon offsets), this approach can be used to finance carbon reduction schemes.

Climate exchanges have been established to provide a spot market in allowances, as well as futures and options market to help discover a market price and maintain liquidity. Currently there are five exchanges trading in carbon allowances: the Chicago Climate Exchange, European Climate Exchange, Nord Pool, PowerNext, and the European Energy Exchange. Carbon prices are normally quoted in Euros per ton of carbon dioxide or its carbon dioxide equivalent ($CO_2e$). Other GHGs (e.g., methane) can also be traded, but nonetheless are quoted as standard multiples of carbon dioxide with respect to their GWP. These features reduce a GHG's cap's financial impact on business, while ensuring that the GHG's limits are met at a national and international level.

As previously disclosed herein, the disclosed methods of diverting MSW from a landfill result in an overall reduction in the emission of a GHG, for example, methane ($CH_4$) and carbon dioxide in comparison to conventional disposal of MSW, for example, in a landfill. Particularly, in the disclosed methods and systems, landfill gas (e.g., comprising methane and carbon dioxide) that would conventionally be produced and lost to the atmosphere (e.g., were the MSW disposed of in a landfill) is not produced and, instead the MSW is advantageously utilized in the disclosed processes, for example, to produce one or more economically-valuable products (e.g., biochar, compressed hydrogen, compressed carbon dioxide, mixed alcohols, and/or FT liquids). Conversely, the instantly disclosed systems and processes produce significantly less carbon dioxide and/or carbon dioxide equivalents than are produced and lost when MSW is disposed of in a landfill (e.g., landfill gas). Thus, the disclosed systems and processes yield a reduction in carbon dioxide and/or carbon dioxide equivalents lost to the atmosphere and, as such, yield reduction in emissions of carbon dioxide and/or u GHG having a carbon dioxide equivalency lost to the atmosphere; that is, the disclosed systems and processes yield a carbon offset.

In an embodiment, the step of quantifying the reduction in emissions of carbon dioxide or a GHG having a carbon dioxide equivalency generally comprises determining (calculating) the difference between the emissions of carbon dioxide and a GHG having a carbon dioxide equivalency that would have been lost to the atmosphere in a conventional process or system (e.g., a process or system where a particular amount of MSW is disposed of in a landfill) and the emissions of carbon dioxide and a GHG having a carbon dioxide equivalency lost to the atmosphere in the performance of one of the disclosed systems.

In an embodiment, the reduction in emissions of carbon dioxide and/or a GHG having a carbon dioxide equivalency may be calculated on a rate basis, for example, on the basis of the rate at which carbon dioxide emissions are reduced with respect to some process variable, for example, a process input (e.g., the amount of MSW processed via the disclosed systems and methods), a process output (e.g., the amount of biochar, compressed hydrogen, compressed carbon dioxide, and/or mixed alcohols produced). The rate at which emissions of carbon dioxide and GHGs having a carbon dioxide equivalency are reduced per unit of process variable may be obtained experimentally and/or by calculating the mass of carbon dioxide and/or GHG having a carbon dioxide equivalency that would be present based upon a compositional and/or stoichiometric relationship to that process variable. By understanding the rate at which emissions of carbon. dioxide and GHGs having a carbon dioxide equivalency are reduced per unit of process variable, it is possible to calculate the total reduction in carbon dioxide emissions (e.g., metric tons of carbon dioxide not emitted over a given duration). Alternatively, the reduction in emissions of carbon dioxide and GHGs having a carbon dioxide equivalency may be determined by monitoring the mass of particular stream.

For example, the reduction in emissions of carbon dioxide or a GHG having a carbon dioxide equivalency may be calculated via a mass balance for a particular mass of MSW diverted from a landfill and introduced into one of the disclosed systems e.g., MSWP systems 100, 200, 300, 400, or 500). In an embodiment, the reduction in emissions of carbon dioxide and/or a GHG having a carbon dioxide equivalency may be a difference in (i) the sum of the carbon dioxide and the carbon dioxide equivalents that would have been produced and released to the atmosphere if that mass of MSW had been disposed of in a landfill and (ii) the sum of the carbon dioxide and the carbon dioxide equivalents that are produced and released to the atmosphere (e.g., flue gases and waste materials) upon processing that mass of MSW via the disclosed system and processes. The reduction in emissions of carbon dioxide and/or a GHG having a carbon dioxide equivalency can be expressed as a mass of carbon dioxide or of a GHG having a carbon dioxide equivalency (e.g., mass of carbon dioxide of the recovered carbon dioxide that was consumed in the fuel production system). The reduction in emissions expressed as a mass of carbon dioxide or a carbon dioxide equivalent can be used for generating at least one carbon credit (e.g., a tradable certificate, permit, or other negotiable instrument) representing the right to emit one metric ton of carbon dioxide or the mass of another GHG having a carbon dioxide equivalency of one metric ton of carbon dioxide. Thus, a reduction of one metric ton in emissions of carbon dioxide or a GHG having a carbon dioxide equivalency can thus be used for generating (e.g., claiming) one carbon credit.

In an embodiment, the systems and methods disclosed herein may achieve a reduction in carbon dioxide and carbon dioxide equivalent emissions of at least 10% (e.g., the mass of carbon dioxide and carbon dioxide equivalents emitted as a result of processing a particular mass of MSW via the disclosed processes and systems is at least 10% less than the mass of carbon dioxide and carbon dioxide equivalents emitted as a result of disposing the same mass of MSW in a landfill), alternatively, a reduction of at least 50%, alternatively, at least 60%, alternatively, at least 70%, alternatively, at least 75%, alternatively, at least 80%, alternatively, at least 85%, alternatively, at least 90%, alternatively, at least 91%, alternatively, at least 92%, alternatively, at least 93%, alternatively, at least 94%, alternatively, at least 95%. For example, in a particular embodiment, the reduction in carbon dioxide and carbon dioxide equivalent emissions ranges from about 70 to about 95%.

In an embodiment, the step of claiming the carbon credit associated with the reduction in emissions of carbon dioxide of the GHG having the carbon dioxide equivalency generally comprises requesting that a suitable carbon-credit-awarding entity award one or more carbon credits on the basis of the reduction in carbon dioxide emissions resulting from the systems and processes disclosed herein. An example of a carbon-credit-awarding entity is the Clean Development Mechanism (CDM), which validates carbon offset projects to ensure they produce actual reductions in carbon dioxide or other GHG emissions.

In an embodiment, an entity that obtains a carbon credit, for example, as disclosed herein, may benefit from both international and national emissions trading mechanisms monetizing those carbon credits on the appropriate climate exchanges. Such monetization would allow such entities to maximize the economic output of the MSWP systems and processes disclosed herein.

EXAMPLES

The following prophetic example provides a quantitative analysis demonstrating the benefits of the proposed systems and processes.

According to the Environmental Protection Agency, 1,000 standard tons (skins) of wet, organic, segregated MSW will release 841 stons of GHGs, comprising about 27%, by weight, methane and about 73% carbon dioxide. Methane has a carbon dioxide equivalency of about 25-times that of carbon dioxide (e.g., methane has about 25 the greenhouse effect in comparison to carbon dioxide). Thus, removing 1,000 tons of MSW from land-filling and keeping the methane out of the atmosphere will avoid the equivalent of 5,620 tons of $CO_2$-equivalentemission as a result of that MSW not being sent to a landfill. Thus, the removed carbon dioxide and carbon dioxide equivalents may constitute a carbon offset and, thus, can by monetized as a carbon credit.

Additionally, the power (e.g., cogenerated power) produced via the disclosed systems and processes may likewise yield a carbon offset. A typical subcritical coal boiler produces about 1,000 stons of carbon dioxide per 1,000 MWhr generated. 1,000 ston/day of wet organic MSW kept from landfills can offset 231 MWe of coal power generation. Thus, 1 ston/day of wet organic MSW removed from landfill is equivalent to 2.2 ston/day of coal feed to boilers. Thus, in this prophetic example, if a local county in USA avoids 1,000 stons per day of MSW from going to a landfill, that enables 231 MWe from a coal fired power plant to continue operating using the carbon credits.

The total MSW produced in US, after sorting, is about 150 MM stons per year (about 400,000 stons per day) of wet MSW. If all this is gasified, the potential coal-fired power plant output that can be sustained is 92,000 MW using the carbon credit from avoiding the use of landfills.

ADDITIONAL EMBODIMENTS

A first embodiment, which is a method of diverting municipal solid waste (MSW) from a landfill comprising receiving, at a MSW processing system, a quantity of MSW, gasifying the quantity of MSW in a gasification unit to yield a syngas stream and biochar stream, converting at least a portion of the syngas to mixed alcohols in an alcohol synthesis unit, separating the mixed alcohols into one or more alcohol products, and determining a carbon offset for diverting the MSW from the landfill to the MSW processing system.

A second embodiment, which is the method of the first embodiment, further comprising, before gasifying the quantity of MSW, separating carbonaceous materials in the MSW from non-carbonaceous materials in the MSW.

A third embodiment, which is the method of one of the first through the second embodiments, further comprising, before gasifying the quantity of MSW, converting the quantity of MSW to a quantity of refuse-derived fuel (RDF).

A fourth embodiment, which is the method of the third embodiment, wherein converting the quantity of MSW to the quantity of RDF comprises shredding, pulverizing, grinding, drying, dehydrating, sterilizing, sizing, screening the MSW, or combinations thereof.

A fifth embodiment, which is the method of one of the first through the fourth embodiments, wherein the MSW has a moisture content at least about 40% by weight when received, and wherein the MSW has a moisture content at least about 40% by weight when introduced into the gasification unit.

A sixth embodiment, which is the method of one of the first through the fifth embodiments, further comprising making at least a portion of the biochar available for purchase.

A seventh embodiment, which is the method of one of the first through the sixth embodiments, further comprising separating a hydrogen gas stream from the syngas stream.

An eighth embodiment, which is the method of the seventh embodiment, further comprising making at least a portion of the hydrogen gas stream available for purchase.

A ninth embodiment, which is the method of one of the first through the eighth embodiments, further comprising separating a carbon dioxide stream from the mixed alcohols.

A tenth embodiment, which is the method of the ninth embodiment, further comprising making at least a portion of the carbon dioxide stream available for purchase.

An eleventh embodiment, which is the method of the ninth embodiment, further comprising returning at least a portion of the carbon dioxide stream to the gasification unit.

A twelfth embodiment, which is the method of one of the first through the eleventh embodiments, further comprising recovering steam from the MSW processing system, and routing the steam to a turbine generator.

A thirteenth embodiment, which is the method of one of the first through the twelfth embodiments, further comprising recovering a recycle gas stream from the alcohol synthesis unit, and returning at least a portion of the recycle gas stream to the gasification unit.

A fourteenth embodiment, which is the method of one of the first through the thirteenth embodiments, wherein the carbon offset is a difference between (i) a sum of a mass of carbon dioxide and carbon dioxide equivalents that would have been produced and released to the atmosphere if the quantity of MSW had been disposed of in the landfill and (ii) a sum of a mass of carbon dioxide and carbon dioxide equivalents produced and released to the atmosphere upon processing the quantity of MSW in the MSW processing system.

A fifteenth embodiment, which is the method of the fourteenth embodiment, further comprising claiming a carbon credit based upon the carbon offset.

A sixteenth embodiment, which is the method of one of the fifteenth embodiment, further comprising offering the carbon credit for sale.

A seventeenth embodiment, which is a method of diverting municipal solid waste (MSW) from a landfill comprising receiving, at a MSW processing system, a quantity of MSW, gasifying the quantity of MSW in a gasification unit to yield a syngas stream and a biochar stream, converting at least a portion of the syngas to a hydrocarbon product stream, wherein the hydrocarbon product stream comprises liquid hydrocarbons, and determining a carbon offset for diverting the MSW from the landfill to the MSW processing system.

An eighteenth embodiment, which is the method of the seventeenth embodiment, further comprising, before gasifying the quantity of MSW, separating carbonaceous materials in the MSW from non-carbonaceous materials in the MSW.

A nineteenth embodiment, which is the method of one of the seventeenth through the eighteenth embodiments, further comprising, before gasifying the quantity of MSW, converting the quantity of MSW to a quantity of refuse-derived fuel (RDF).

A twentieth embodiment, which is the method of the nineteenth embodiment, wherein converting the quantity of MSW to the quantity of RDF comprises shredding, pulverizing, grinding, drying, dehydrating, sterilizing, sizing, screening the MSW, or combinations thereof.

A twenty-first embodiment, which is the method of one of the seventeenth through the twentieth embodiments, wherein the MSW has a moisture content at least about 40% by weight when received, and wherein the MSW has a moisture content at least about 40% by weight when introduced into the gasification unit.

A twenty-second embodiment, which is the method of one of the seventeenth through the twenty-first embodiments, further comprising making at least a portion of the biochar available for purchase.

A twenty-third embodiment, which is the method of one of the seventeenth through the twenty-second embodiments, further comprising separating a hydrogen gas stream from the syngas stream.

A twenty-fourth embodiment, which is the method of the twenty-third embodiment, further comprising making at least a portion of the hydrogen gas stream available for purchase.

A twenty-fifth embodiment, which is the method of one of the seventeenth through the twenty-fourth embodiments, wherein converting at least a portion of the syngas to the hydrocarbon product stream comprises a Fischer-Tropsch process.

A twenty-sixth embodiment, which is the method of one of the seventeenth through the twenty-fifth embodiments, further comprising converting paraffins in the hydrocarbon product stream to liquid hydrocarbons.

A twenty-seventh embodiment, which is the method of the twenty-sixth embodiment, wherein converting paraffins to liquid hydrocarbons comprises introducing at least a portion of the hydrocarbon product stream into a hydrocracking unit.

A twenty-eighth embodiment, which is the method of one of the seventeenth through the twenty-seventh embodiments, further comprising offering at least a portion of liquid hydrocarbons available for purchase.

A twenty-ninth embodiment, which is the method of one of the seventeenth through the twenty-eighth embodiments, further comprising recovering steam from the MSW processing system and routing the steam to a turbine generator.

A thirtieth embodiment, which is the method of one of the seventeenth through the twenty-ninth embodiments, wherein the carbon offset is a difference between (i) a sum of a mass of carbon dioxide and carbon dioxide equivalents that would have been produced and released to the atmosphere if the quantity of MSW had been disposed of in the landfill and (ii) a sum of a mass of carbon dioxide and carbon dioxide equivalents produced and released to the atmosphere upon processing the quantity of MSW in the MSW processing system.

A thirty-first embodiment, which is the method of one of the seventeenth through the thirtieth embodiments claim 17, further comprising claiming a carbon credit based upon the carbon offset.

A thirty-second embodiment, which is the method of the thirty-first embodiment, further comprising offering the carbon credit for sale.

A thirty-third embodiment, which is a method comprising receiving a feed stream of municipal solid waste (MSW), optionally drying the MSW, gasifying a quantified amount of the MSW in a gasification unit and recovering a syngas product stream and a biochar product stream, wherein the gasified MSW has a landfill methane equivalent, generating a negotiable credit based upon the landfill methane equivalent of the quantified amount of gasified MSW, optionally altering a hydrogen to carbon monoxide ratio of at least a portion of the syngas product stream, converting at least a portion of the syngas to mixed alcohols or Fischer-Tropsch (FT) liquids, and separating the mixed alcohols or FT liquids into one or more salable products.

A thirty-fourth embodiment, which is a method comprising receiving a feed stream of municipal solid waste (MSW), optionally drying the MSW, gasifying a quantified amount of the MSW in a gasification unit and recovering a syngas product stream and a biochar product stream, calculating a negotiable credit based upon a landfill methane equivalent of the quantified amount of the gasified MSW, optionally altering a hydrogen to carbon monoxide ratio of at least a portion of the syngas product stream, converting at least a portion of the syngas to mixed alcohols or FT liquids, and separating the mixed alcohols or FT liquids into one or more salable products.

A thirty-fifth embodiment, which is a method comprising receiving a feed stream of municipal solid waste (MSW), drying the MSW to produce dried MSW, gasifying a quantified amount of the dried MSW in a gasification unit and recovering a syngas product stream and a biochar product stream, calculating a negotiable credit based upon a landfill methane equivalent of the gasified MSW, altering a hydrogen to carbon monoxide ratio of at least a portion of the syngas product stream and recovering a hydrogen product stream and an adjusted syngas stream, feeding at least a portion of the adjusted syngas to a mixed alcohols production unit to produce mixed alcohols, recycling carbon dioxide from the mixed alcohols production unit to the gasification unit, and separating the mixed alcohols into one or more salable products.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A method of diverting municipal solid waste (MSW) from a landfill comprising:
   receiving, at a MSW processing system, a quantity of MSW;
   gasifying the quantity of MSW in a gasification unit to yield a syngas stream and biochar stream;
   converting at least a portion of the syngas to mixed alcohols in an alcohol synthesis unit;
   generating a carbon dioxide off-gas stream from the alcohol synthesis unit,
   separating a carbon dioxide stream from the carbon dioxide off-gas stream;
   recycling at least a portion of the carbon dioxide stream to the gasification unit;
   separating the mixed alcohols into one or more alcohol products; and
   determining a carbon offset for diverting the MSW from the landfill to the MSW processing system.

2. The method of claim 1, further comprising, before gasifying the quantity of MSW, separating carbonaceous materials in the MSW from non-carbonaceous materials in the MSW.

3. The method of claim 1, further comprising, before gasifying the quantity of MSW, converting the quantity of MSW to a quantity of refuse-derived fuel (RDF).

4. The method of claim 3, wherein converting the quantity of MSW to the quantity of RDF comprises shredding, pulverizing, grinding, drying, dehydrating, sterilizing, sizing, screening the MSW, or combinations thereof.

5. The method of claim 1,
   wherein the MSW has a moisture content at least about 40% by weight when received, and
   wherein the MSW has a moisture content at least about 40% by weight when introduced into the gasification unit.

6. The method of claim 1, further comprising making at least a portion of the biochar available for purchase.

7. The method of claim 1, further comprising separating a hydrogen gas stream from the syngas stream.

8. The method of claim 7, further comprising making at least a portion of the hydrogen gas stream available for purchase.

9. The method of claim 1, further comprising making at least a portion of the carbon dioxide stream available for purchase.

10. The method of claim 1, further comprising:
    recovering steam from the MSW processing system; and
    routing the steam to a turbine generator.

11. The method of claim 1, further comprising:
    recovering a recycle gas stream from the alcohol synthesis unit; and
    returning at least a portion of the recycle gas stream to the gasification unit.

12. The method of claim 1, wherein the carbon offset is a difference between (i) a sum of a mass of carbon dioxide and carbon dioxide equivalents that would have been produced and released to the atmosphere if the quantity of MSW had been disposed of in the landfill and (ii) a sum of a mass of carbon dioxide and carbon dioxide equivalents produced and released to the atmosphere upon processing the quantity of MSW in the MSW processing system.

13. The method of claim 12, further comprising claiming a carbon credit based upon the carbon offset.

14. The method of claim 13, further comprising offering the carbon credit for sale.

15. A method comprising:
receiving a feed stream of municipal solid waste (MSW);
gasifying a quantified amount of the MSW in a gasification unit and recovering a syngas product stream and a biochar product stream, wherein the gasified MSW has a landfill methane equivalent;
generating a negotiable credit based upon the landfill methane equivalent of the quantified amount of gasified MSW;
separating a hydrogen gas stream from the syngas product stream to produce a syngas stream;
altering a hydrogen to carbon monoxide ratio of at least a portion of the syngas product stream based on separating the hydrogen gas stream from the syngas product stream;
converting at least a portion of the syngas in the syngas stream to mixed alcohols or Fischer-Tropsch (FT) liquids in a synthesis unit;
generating a carbon dioxide off-gas stream from the synthesis unit
separating a carbon dioxide stream from the carbon dioxide off-gas stream; and
recycling at least a portion of the carbon dioxide stream to the gasification unit; and
separating the mixed alcohols or FT liquids into one or more salable products.

16. A method comprising:
receiving a feed stream of municipal solid waste (MSW);
gasifying a quantified amount of the MSW in a gasification unit and recovering a syngas product stream and a biochar product stream, wherein the gasification unit is externally heated;
calculating a negotiable credit based upon a landfill methane equivalent of the quantified amount of the gasified MSW;
converting at least a portion of the syngas to mixed alcohols or FT liquids in a synthesis unit;
generating a carbon dioxide off-gas stream from the synthesis unit;
separating a carbon dioxide stream from the carbon dioxide off-gas stream;
recycling at least a portion of the carbon dioxide stream to the gasification unit; and
separating the mixed alcohols or FT liquids into one or more salable products.

17. The method of claim 16, further comprising: carrying out the gasifying in the substantial absence of internal combustion of the MSW in the gasification unit.

18. The method of claim 16, further comprising:
separating a hydrogen gas stream from the syngas product stream; and
altering a hydrogen to carbon monoxide ratio of at least a portion of the syngas product stream based on separating the hydrogen gas stream from the syngas product stream.

* * * * *